United States Patent
Coe, Jr. et al.

(10) Patent No.: US 11,607,135 B1
(45) Date of Patent: Mar. 21, 2023

(54) LOW NOISE RESPONSE DETECTION USING OPTICAL PROBE

(71) Applicants: IR MEDTEK LLC, Gahanna, OH (US); OHIO STATE INNOVATION FOUNDATION, Columbus, OH (US)

(72) Inventors: James V. Coe, Jr., Dublin, OH (US); Rebecca C. Bradley, Gahanna, OH (US)

(73) Assignees: IR MEMTEK LLC, Gahanna, OH (US); OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 17/810,868

(22) Filed: Jul. 6, 2022

(51) Int. Cl.
  *A61B 5/00* (2006.01)
  *G01N 21/3563* (2014.01)
  *G01N 21/39* (2006.01)

(52) U.S. Cl.
  CPC ....... *A61B 5/0075* (2013.01); *G01N 21/3563* (2013.01); *G01N 21/39* (2013.01)

(58) Field of Classification Search
  CPC ... A61B 5/0075; G01N 21/3563; G01N 21/39
  See application file for complete search history.

(56) References Cited

U.S. PATENT DOCUMENTS

2009/0069871 A1* 3/2009 Mahadevan-Jansen ..................... A61N 5/0618 607/92

\* cited by examiner

*Primary Examiner* — Kiho Kim
(74) *Attorney, Agent, or Firm* — Schwegman Lundberg & Woessner, P.A.

(57) ABSTRACT

Signal processing techniques that can include an embedded software low-noise response pulse detection, which can help provide an enhanced signal-to-noise characteristic, such as can help permit highly specific fast IR spectroscopic tissue analysis. Using a difference between (1) response signal values during a first time period duration of a response pulse from a tissue sample illuminated by illumination pulse, and (2) response signal values for a similar first time period duration between response pulses, for a low duty cycle (e.g., less than 50%, 10% or even at about 5% duty cycle) illumination pulse, accumulation of noise in the response signal between electromagnetic illumination pulses can be limited. In particular, the described signal pre-processing techniques can help extract meaningful information for performing spectroscopic analysis and characterization of the tissue sample despite amplitude and temporal variations that can be encountered when using the system.

21 Claims, 9 Drawing Sheets

LOW NOISE RESPONSE DETECTION USING OPTICAL PROBE

TECHNICAL FIELD

This document pertains generally, but not by way of limitation, to optical spectroscopic tissue characterization such as for cancer detection or diagnosis, and more particularly, but not by way of limitation, to configuring signal processing circuitry including software-enabled low noise response detection for use with an optical probe.

BACKGROUND

Coe et al. U.S. Patent Application Publication No. US 2019/0110687 A1 entitled SYSTEM AND METHOD FOR THE DISCRIMINATION OF TISSUES USING A FAST INFRARED CANCER PROBE, which is hereby incorporated herein by reference, and which published on Apr. 18, 2019, relates to using an infrared probe and discriminating software to rapidly discriminate normal non-cancerous tissue from abnormal cancerous tissue.

SUMMARY

Infrared (IR) illumination of a tissue sample can be used to perform spectroscopic analysis of the tissue sample, such as to detect or diagnose cancer or another tissue characteristic. One or more tunable quantum cascade laser (QCLs) can be used to perform the IR illumination of the tissue sample, such as via a crystal tip or a Fiber Loop Probe placed against the tissue sample. Tuning one or more QCLs to scan various illumination wavelengths or wavenumbers, a probe response signal from the tissue sample can be detected, acquired, and analyzed, such as to determine one or more characteristics of the tissue sample. A QCL can exhibit a large degree of amplitude variability in issued laser pulses. Moreover, noise can be present in both the illumination and detection sides of the spectroscopic system. This document describes, among other things, signal processing techniques that can include an embedded software low noise response pulse detection, which can help provide an enhanced signal-to-noise characteristic, such as can help permit highly specific fast IR spectroscopic tissue analysis.

For example, the signal processing techniques described herein can include an embedded software low-noise response pulse detection, which can help provide an enhanced signal-to-noise characteristic, such as can help permit highly specific fast IR spectroscopic tissue analysis. Using a difference between (1) response signal values during a first time period duration of a response pulse from a tissue sample illuminated by illumination pulse, and (2) response signal values for a similar first time period duration between response pulses, for a low duty cycle (e.g., less than or equal to 50 percent, 10 percent, or even at about 5 percent duty cycle) illumination pulse, accumulation of noise in the response signal between electromagnetic illumination pulses can be limited. In particular, the described signal pre-processing techniques can help extract meaningful information for performing spectroscopic analysis and characterization of the tissue sample despite amplitude and temporal variations that can be encountered when using the system.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, signal processing techniques that can include an embedded software low noise response pulse detection, which can help provide an enhanced signal-to-noise characteristic, such as can help permit highly specific fast IR spectroscopic tissue analysis.

For example, the signal processing techniques described herein can include an embedded software low-noise response pulse detection, which can help provide an enhanced signal-to-noise characteristic, such as can help permit highly specific fast IR spectroscopic tissue analysis.

Using a difference between (1) response signal values during a first time period duration of a response pulse from a tissue sample illuminated by illumination pulse, and (2) response signal values for a similar first time period duration between response pulses, for a low duty cycle (e.g., less than 50%, 10% or even at about 5% duty cycle) illumination pulse, accumulation of noise in the response signal between electromagnetic illumination pulses can be limited. In particular, the described signal pre-processing techniques can help extract meaningful information for performing spectroscopic analysis and characterization of the tissue sample despite amplitude and temporal variations that can be encountered when using the system.

Figure 1:
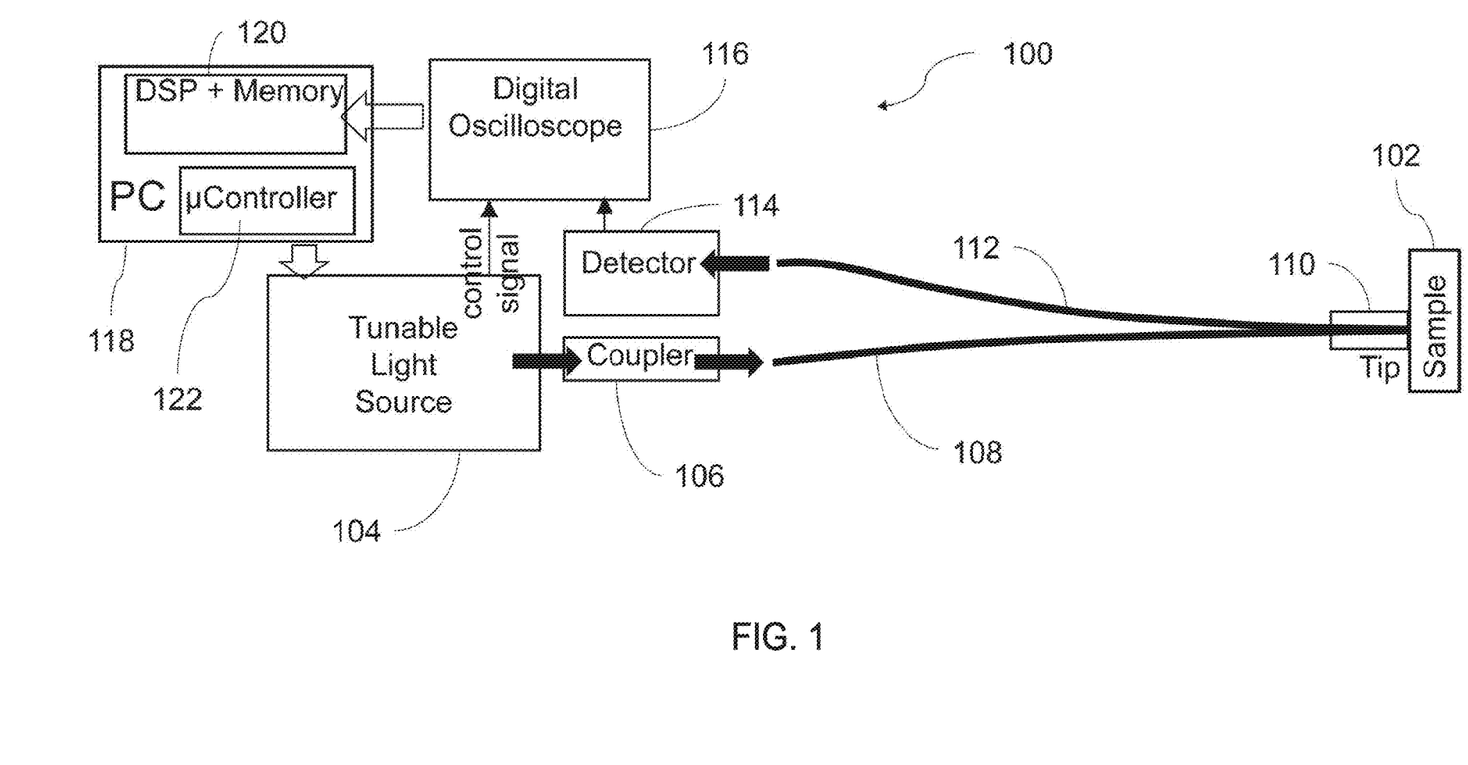
FIG. 1 is a schematic/block diagram illustrating an example of portions of a system that can be used for spectroscopic analysis and classification or other characterization of a tissue sample of interest, such as for cancer detection or for characterizing one or more other tissue attributes.

FIG. 1 is a schematic/block diagram illustrating an example of portions of a system 100 that can be used for spectroscopic analysis and classification or other characterization of a tissue sample 102 of interest, such as for cancer detection or for characterizing one or more other tissue attributes. The system 100 can include a tunable light source 104, such as to illuminate the sample with electromagnetic energy such as for eliciting one or more of an absorption, scattering, reflection, fluorescence, Raman, or other response signal of interest from the sample 102. In an illustrative example, the light source 104 can include tunable laser system, such as which can include a single or multiple (e.g., two) Quantum Cascade Lasers (QCLs), such as can issue illumination pulses at specified wavenumbers, such as to cover a range between 1340 and 1870 $cm^{-1}$, such as in 54 steps of 10 $cm^{-1}$ for each of the two QCLs. The light source 104 can be coupled via an optical coupler 106 into an illumination optical fiber 108 for communication to an Attenuated Total Reflection (ATR) probe loop or crystal tip 110 that can be located against or near the sample 102. For example, the optical coupler 106 can include an optocoupler, such as with a focal length of f=50 mm, such as with an SMA connector. The ATR loop probe tip 110 can be obtained from Art Photonics, such as a detachable single PIR-Loops AP10109. The response signal can be communicated from the sample 102 via the ATR probe loop tip 110 and a response optical fiber 112 to a photodetector 114, such as a Vigo MCT Detector, PVM-10.6-1x1, for being detected and transduced into an electrical response signal representative of the optical response signal from the tip 110. The resulting electrical response signal can be buffered or amplified (e.g., using a Vigo amplifier and power supply SIP-DC-100M-G, PPS-03) and communicated from the detector 114 to a digital oscilloscope 116 such as for sampling, digitization, and storage into a memory buffer of the digital oscilloscope 116. In an example, the digital oscilloscope can include a Picoscope 4224, which can provide a deep memory. The buffered digital response samples can be communicated from the digital oscilloscope 116 to a computer 118, such as can include processor circuitry that can be configured to include or provide Digital Signal Processing (DSP) circuitry 120 and memory circuitry. The DSP circuitry 120 can receive the buffered digital response samples from the digital oscilloscope 116 and can process the digital response samples such as to perform signal processing and spectroscopic analysis on the tissue sample 102. The computer 118 can also be configured to include or provide a microcontroller 122, such as can be used to control the tunable light source 104.

Figures 2A, 2B:
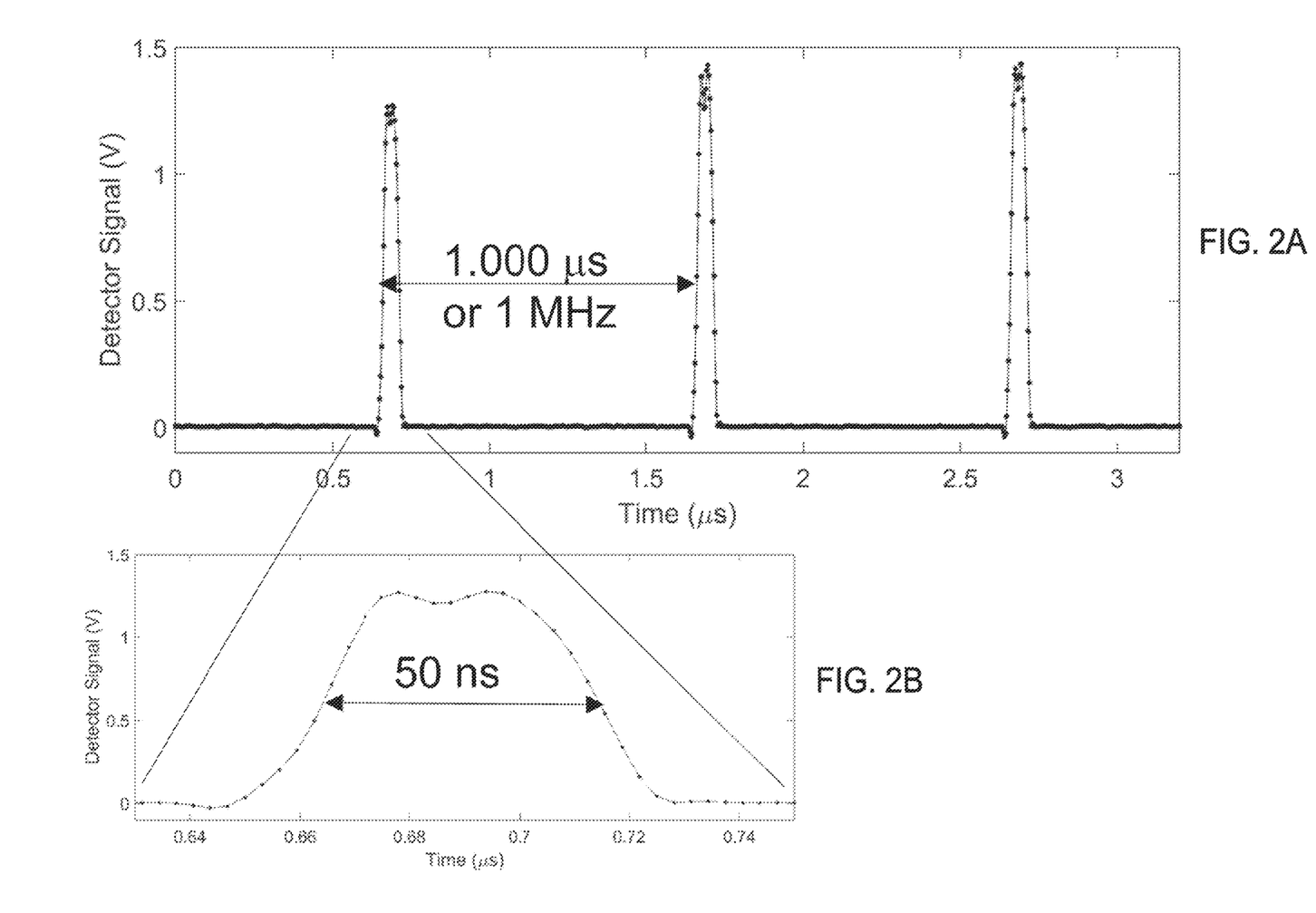
FIG. 2A shows an example of a resulting electrical response signal output from the detector amplitude (V) vs. time (microseconds) in response to a series of illumination pulses issued by the tunable light source.
FIG. 2B shows an example of a zoomed-in portion of the signal shown in FIG. 2A, illustrating the electrical response signal corresponding to the first issued illumination pulse of FIG. 2A.

FIG. 2A shows an example of a resulting electrical response signal output from the detector 114 amplitude (V) vs. time (microseconds) in response to a series of illumination pulses issued by the tunable light source 104, such as a Block LaserTune, such as which can be configured, in an illustrative example, to provide 54 wavenumber steps of 10 $cm^{-1}$, such as with a 100 ns pulsewidth, 5 milliseconds between steps, with a 1.6 microsecond period, such as at 625 KHz and a 6.25% Duty Cycle. FIG. 2A shows an illustrative example of the electrical response signal with 1.000 microseconds between illumination pulses, which corresponds to a 1 MHz illumination pulse repetition rate, and a 1650 $cm^{-1}$ wavenumber and a 5% Duty Cycle.

FIG. 2B shows an example of a zoomed-in portion of the signal shown in FIG. 2A, illustrating the electrical response signal corresponding to the first issued illumination pulse of FIG. 2A.

Figure 3A:
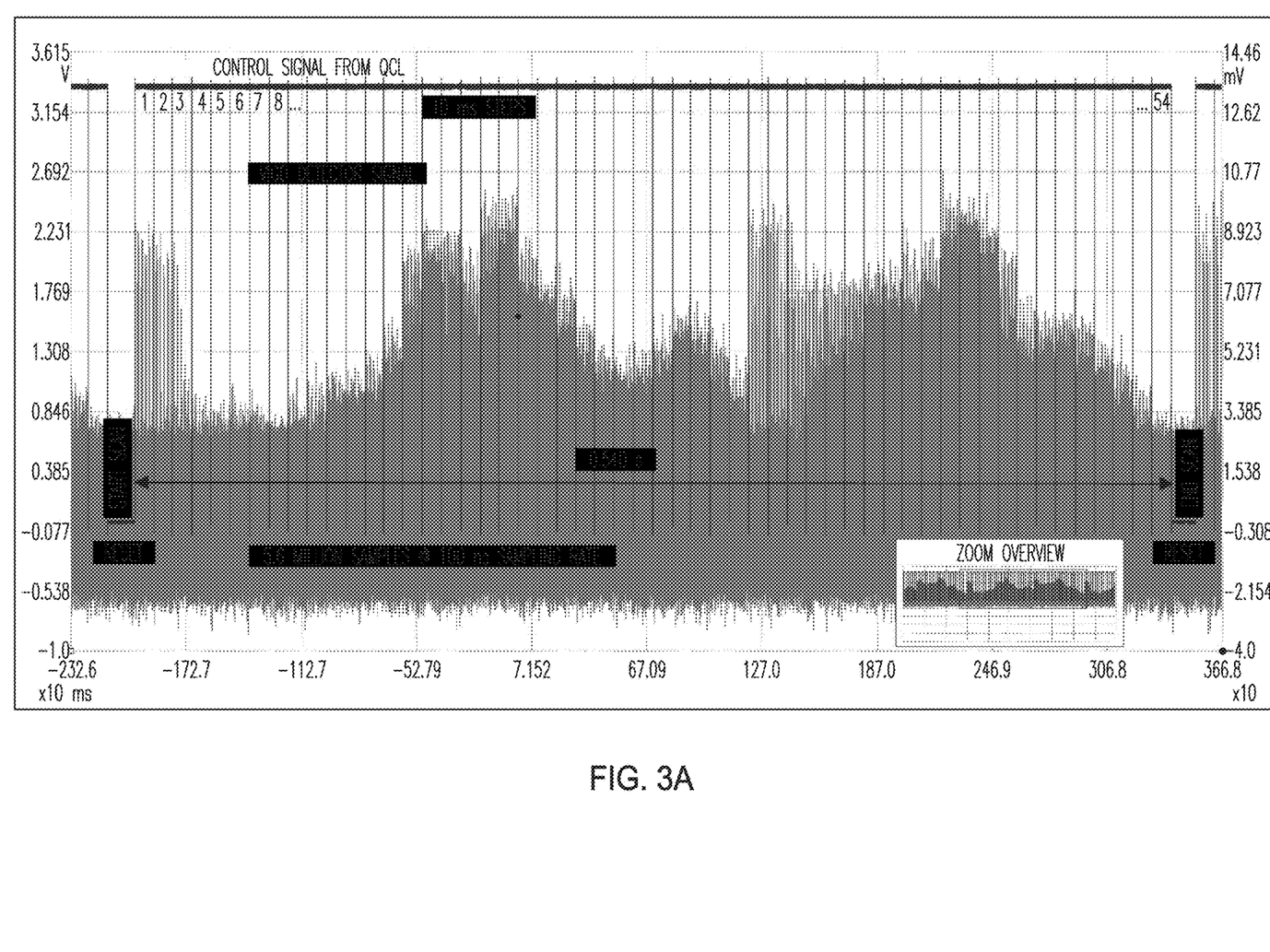
FIG. 3A shows an illustrative example of the electrical response signal (amplitude vs. time) as digitized and sampled by the digital oscilloscope, with a control signal from the tunable light source to the digital oscilloscope superimposed thereupon.

FIG. 3A shows an illustrative example of the electrical response signal (amplitude vs. time) as digitized and sampled by the digital oscilloscope 116, with a control signal from the tunable light source 104 to the digital oscilloscope 116 superimposed thereupon. In this example, the control signal demonstrates an example in which a scan is started (control signal goes low), followed by issuing a specified number of illumination pulses at a specified wavenumber for a specified duration (e.g., 10 milliseconds), after which the tunable light source 104 is incremented (or decremented) to the next specified wavenumber for a similar specified duration to similarly issue a specified number of illumination pulses at the new specified wavenumber for the corresponding specified duration. In this manner, as seen in FIG. 3A, the wavenumber can be stepped across a specified range of wavenumbers, which is shown as 54 steps of different specified wavenumbers in the illustrative example shown in FIG. 3, with a total scan curation of 0.540 seconds to complete these 54 steps. The resulting electrical response signal data is shown in this illustrative example as being captured at a 100 nanosecond sampling rate, resulting in 5.6 million samples corresponding to the scan over the 54 steps of different specified wavenumbers.

Figure 3B:
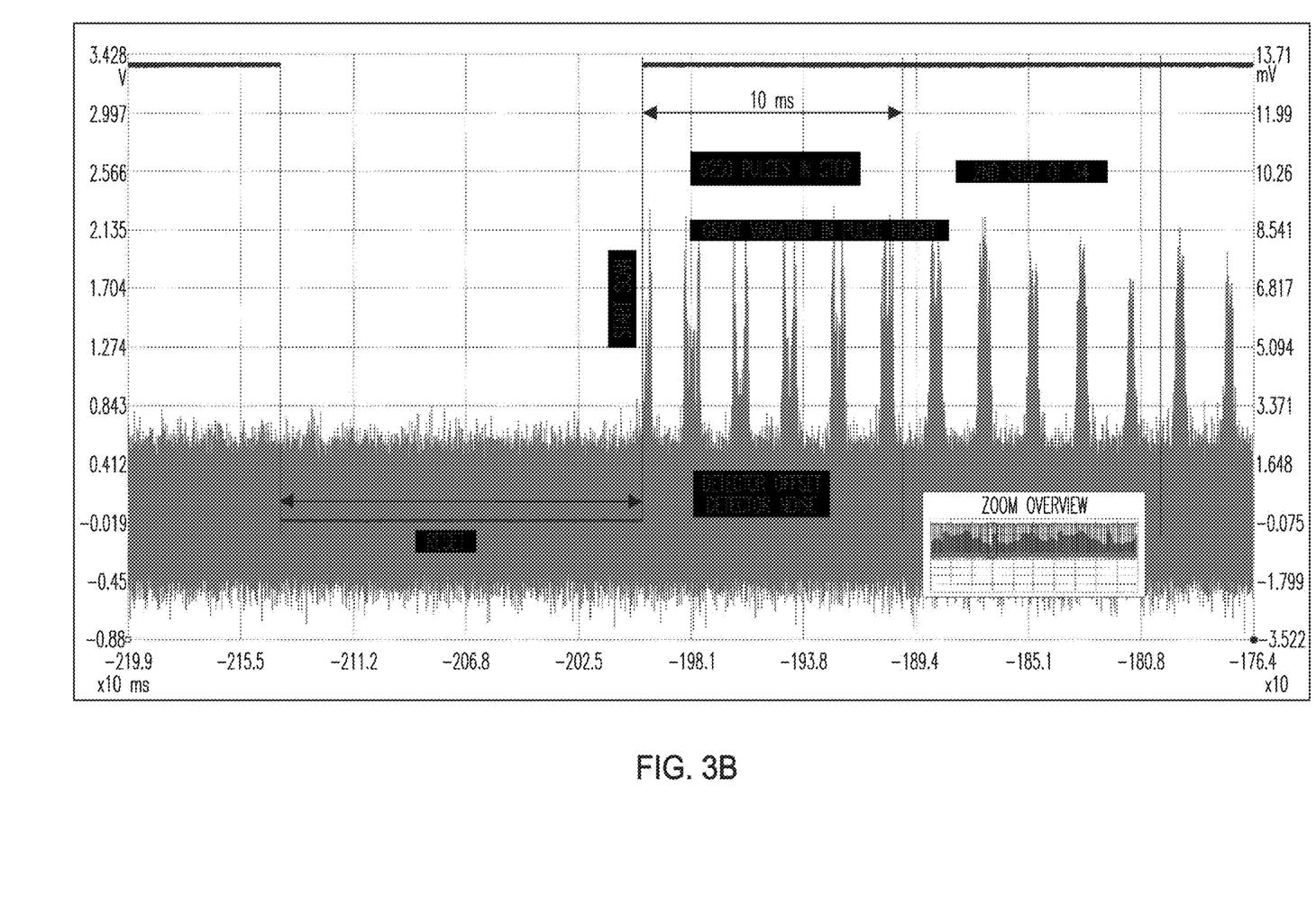
FIG. 3B shows a zoomed in portion of the electrical response signal shown in FIG. 3A.

FIG. 3B shows a zoomed in portion of the electrical response signal shown in FIG. 3A. FIG. 3B shows an example at the beginning of the scan, zooming in on the first two steps of 54 steps between specified wavenumbers. In this illustrative example, 6250 pulses are issued in each step at a particular specified wavenumber, before stepping to the next specified wavenumber in the scan across the 54 steps of different specified wavenumbers. From FIG. 3B, both offset and noise resulting from the detector 114 are observed. FIG. 3B also shows an illustrative example of the significant potential variation in illumination pulse amplitude, resulting in variability in the electrical response signal amplitude as shown in FIG. 3B, such that processing of a number (e.g., 6250, in this illustrative example) of response pulses is helpful for accurately determining the response from the tissue sample 102 at a particular specified wavenumber.

Figure 3C:
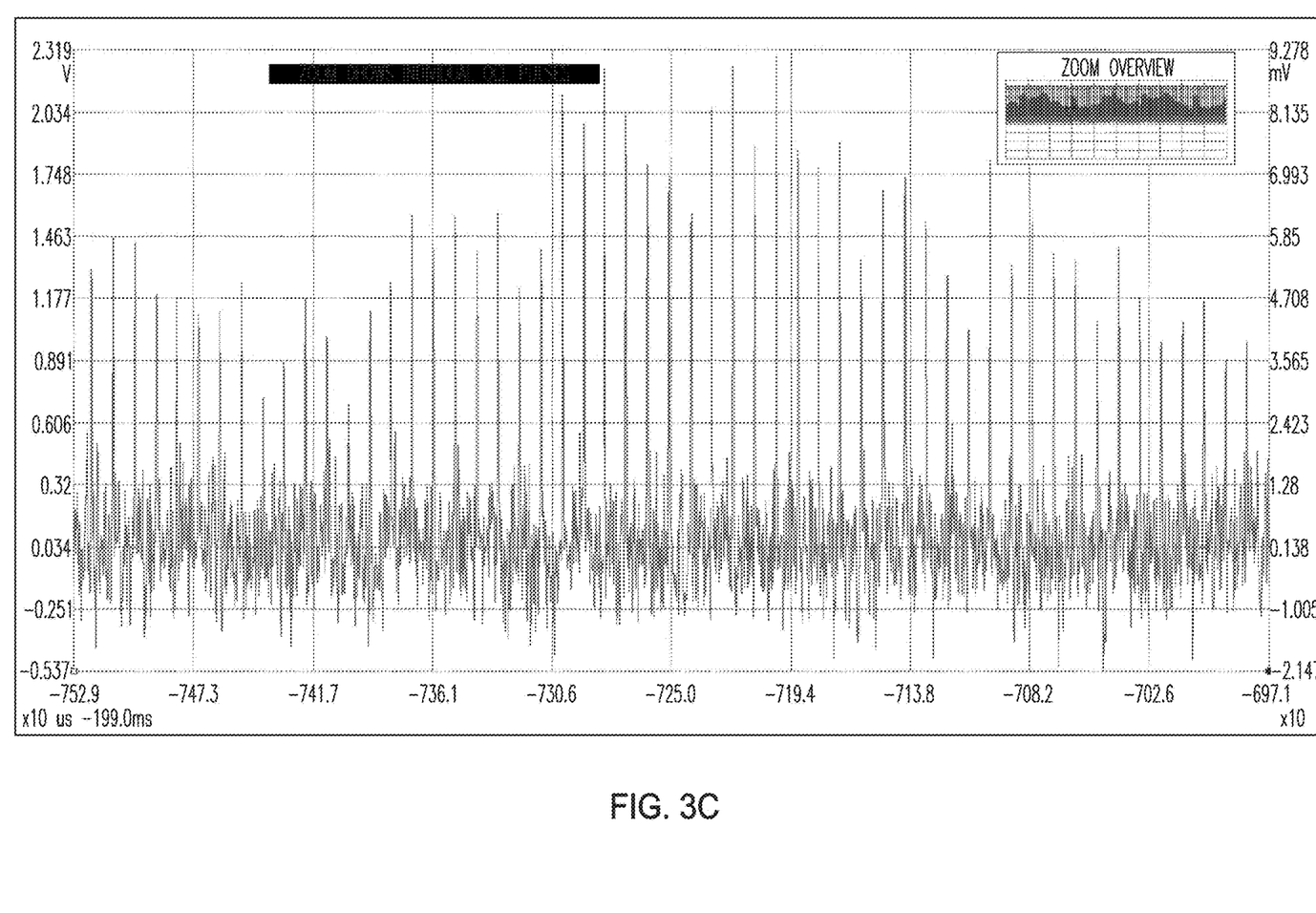
FIG. 3C shows a further zoomed in portion of the electrical response signal shown in FIG. 3B.

FIG. 3C shows a further zoomed in portion of the electrical response signal shown in FIG. 3B. In FIG. 3C, the digitized samples of the electrical response signal corresponding to individual QCL illumination pulses is shown, further demonstrating the problem of amplitude variability in the electrical response signal arising from amplitude variability in the issued individual QCL illumination pulses. To help accurately and efficiently process the resulting electrical response signal and to help permit useful spectroscopic analysis and characterization of the tissue sample 102, particular signal pre-processing techniques can be employed, such as described in detail herein.

Figure 4:
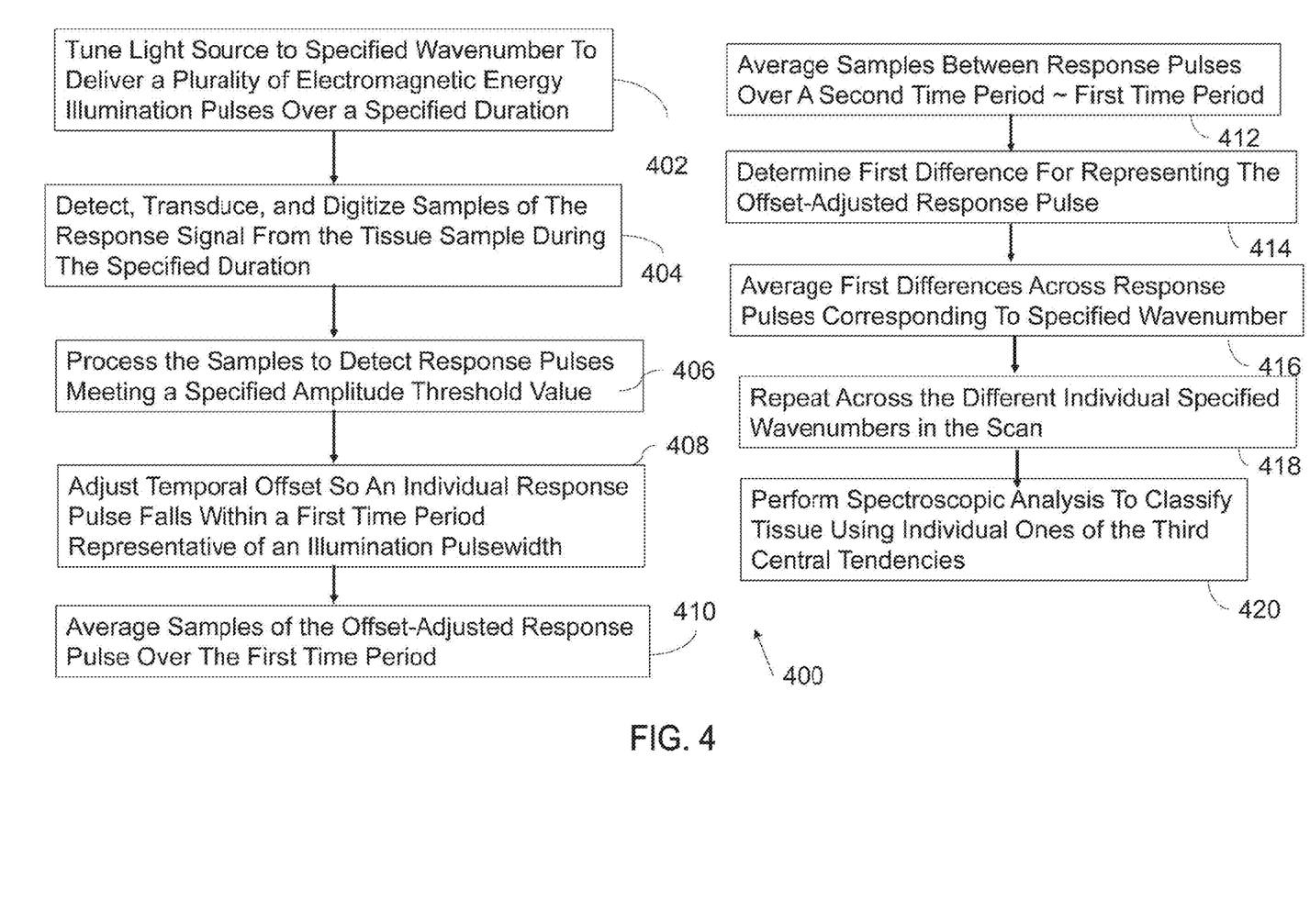
FIG. 4 is a flow block diagram illustrating generally aspects of portions of a technique, including particular signal pre-processing techniques that can help extract meaningful information for performing spectroscopic analysis and characterization of the tissue sample despite amplitude and temporal variations that can be encountered when using the system.

FIG. 4 is a flow block diagram illustrating generally aspects of portions of a technique 400, including particular signal pre-processing techniques that can help extract meaningful information for performing spectroscopic analysis and characterization of the tissue sample 102 despite amplitude and temporal variations that can be encountered when using the system 100.

At 402, the microcontroller 122 can be used to tune the tunable light source 104 to a specified wavenumber to deliver a plurality of electromagnetic energy pulses to the tissue sample 102 over a specified duration. For example, this can include performing a scan over 54 different specified wavenumbers, and delivering a significant number (e.g., 6250) of illumination pulses at a particular specified wavenumber over a specified duration of 10 milliseconds, before stepping to the next specified wavenumber (consecutive or non-consecutive) in the sequence of the scan. The method can include synchronizing the detecting and transducing the response signal from the tissue sample to a Start Scan control signal used by a laser to start a scan across different wavenumbers and/or synchronizing to a Start Wavenumber Step control signal used by the laser to start issuing pulses at a specified wavenumber.

At 404, the optical response signal from the tissue sample 102 can be detected, transduced into an electrical response signal, and digitized and stored, such as using the ATR probe tip 110, the detector 114, and the digital oscilloscope 116 shown in FIG. 1.

At 406, the digitized samples can be digitally processed. This can include detecting electrical response pulses (corresponding to the illumination pulses) such as by comparing the digitized samples to a specified amplitude threshold value, such as using the DSP circuitry 120 as shown in FIG. 1. Portions of the detected electrical response signal samples exceeding the specified amplitude threshold value can be deemed to correspond to the illumination pulses, while other portions of the detected electrical response signal samples not exceeding the specified amplitude threshold value can be deemed to correspond to noise in the electrical response signal, such as can arise from the detector 114 or elsewhere, for example.

At 408, an individual electrical response pulse (corresponding to a particular illumination pulse) can be offset-adjusted, such as using the DSP circuitry 120 as shown in FIG. 1. This can include adjusting a temporal offset such that the individual electrical response pulse falls within a first time period (e.g., 50 nanoseconds) representative of an illumination pulsewidth, e.g., of the illumination pulse issued by the QCL or other light source 104. This offset-adjustment is described in more detail elsewhere herein.

At 410, a first central tendency (e.g., mean, median, or the like) of the electrical response signal samples including the offset-adjusted response pulse (corresponding to a particular illumination pulse) can be determined, such as over the first time period (e.g., 50 nanoseconds) representative of the illumination pulsewidth, such as using the DSP circuitry 120 as shown in FIG. 1.

At 412, as second central tendency (e.g., mean, median, or the like) of electrical response signal samples occurring between successive response pulses (with each response pulse corresponding to a particular illumination pulse) can be determined, such as using the DSP circuitry 120 as shown in FIG. 1. The electrical response signal samples occurring between successive response pulses can be taken over a second time period that is approximately equal to the first time period representative of the illumination pulsewidth corresponding to a particular illumination pulse.

At 414, a first difference between the first and second central tendencies can be determined and used for representing a particular response pulse (corresponding to a particular illumination pulse), such as using the DSP circuitry 120 such as shown in FIG. 1.

At 416, a third central tendency (e.g., mean, median, or the like) of individual ones of the first differences can be computed, such as using the DSP circuitry 120 such as shown in FIG. 1. The determined third central tendency of individual ones of the first differences corresponding to a plurality of the offset-adjusted response pulses at the specified wavenumber can be used for representing the response signal at that particular specified wavenumber.

At 418, the acts 402-416 can be repeated, as the scan steps to another specified wavenumber, across the various different specified wavenumbers in the scan over the specified wavenumber range. This can produce a plurality of third central tendencies, with individual ones corresponding to individual ones of the specified wavenumbers in the specified wavenumber range of the scan.

At 420, specified individual ones or all of the plurality of third central tendencies can be used to perform spectroscopic analysis to classify the tissue sample 102. The signal-preprocessing described herein and performed before performing such spectroscopic analysis at 420 can help improve the accuracy of the spectroscopic analysis and tissue characterization, such as by accounting for and reducing the effects of amplitude and temporal variability in the issued illumination pulses, the corresponding detected response pulses, or both. The spectroscopic analysis and tissue characterization can be performed using a trained learning model, such as using the Support Vector Machines (SVM) technique or other analytic techniques such as described in Coe et al. U.S. Patent Application Publication No. US 2019/0110687 A1 entitled SYSTEM AND METHOD FOR THE DISCRIMINATION OF TISSUES USING A FAST INFRARED CANCER PROBE, which is incorporated herein by reference.

Figure 5:
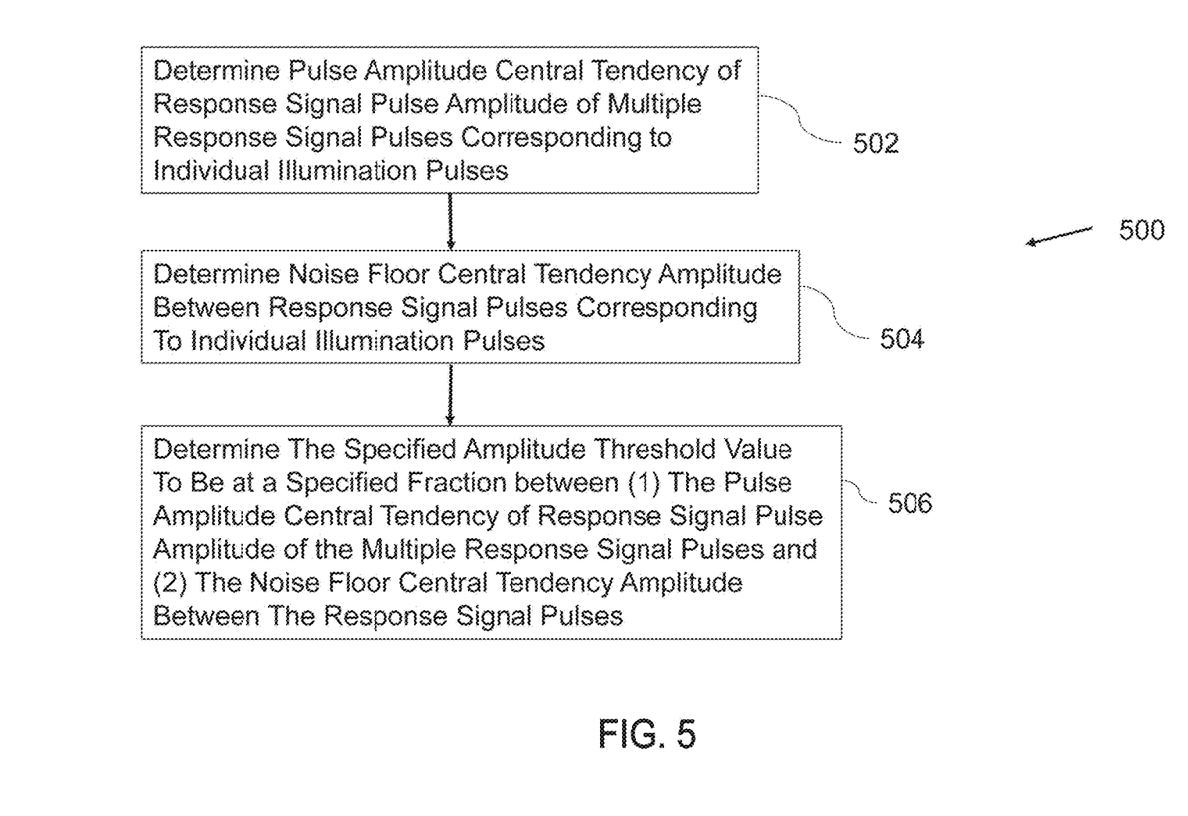
FIG. 5 is a flow block diagram illustrating generally aspects of portions of a technique for establishing a specified amplitude threshold value.

FIG. 5 is a flow block diagram illustrating generally aspects of portions of a technique 500 for establishing a specified amplitude threshold value, such as used at 406 in FIG. 4.

At 502, a central tendency of response signal pulse amplitudes of multiple (e.g., several, tens, hundreds) response signal pulses corresponding to individual illumination pulses (e.g., for the same specified wavenumber or over different specified wavenumbers) can be determined using the DSP circuitry 120, such as using the corresponding electrical response signal samples for the response signal pulses (corresponding to individual illumination pulses)

At 504, a noise floor central tendency of "noise" amplitudes between response signal pulses can be determined using the DSP circuitry 120, such as using multiple (e.g., several, tens, hundreds) noise sample periods, such as having durations corresponding to the durations used for sampling the response signal pulses.

At 506, a specified amplitude threshold value can be determined, such as to be at a specified fraction between (1) the response pulse amplitude central tendency of response signal pulse amplitude of the multiple response signal pulses of 502 and (2) the noise floor central tendency amplitude between the response signal pulses of 504. As an illustrative example, the specified fraction can be one-half, such that the specified amplitude threshold value is at a midpoint between the noise floor central tendency and the response pulse amplitude central tendency. The specified threshold can be used to detect response pulses meeting the specified amplitude threshold value.

Figure 6:
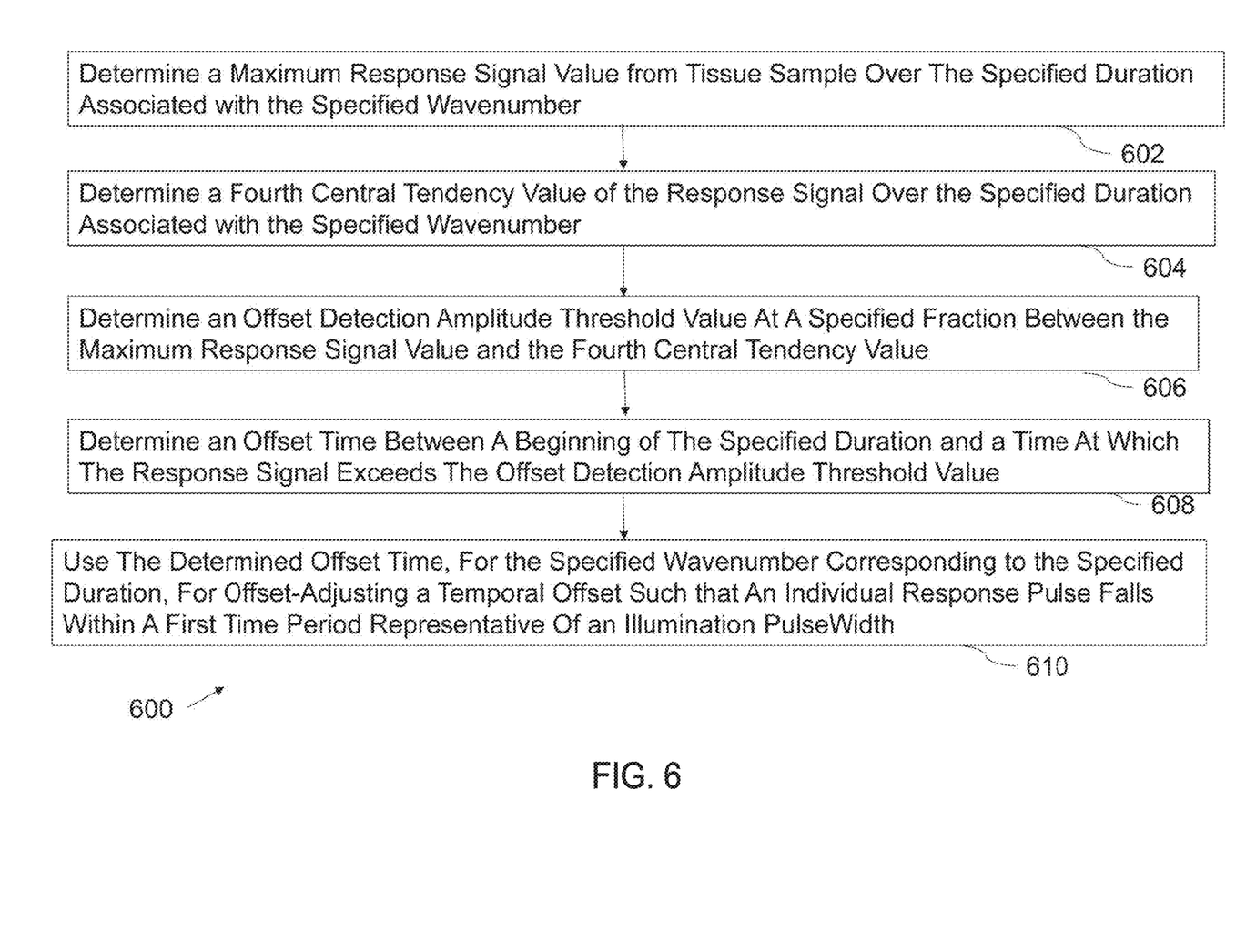
FIG. 6 is a flow block diagram illustrating generally aspects of portions of a technique for offset-adjusting a temporal offset such that an individual response pulse falls within a first time period representative of the illumination pulsewidth.

FIG. 6 is a flow block diagram illustrating generally aspects of portions of a technique 600 for offset-adjusting a temporal offset such that an individual response pulse falls within a first time period representative of the illumination pulsewidth, such as used at 408 in FIG. 4. As an initial note, such offset-adjusting can be helpful because there can be temporal jitter in the issuance of illumination pulses by the tunable light source 104. Even though, at 406, response pulses can be detected by comparing the response signal amplitude to a specified threshold value to detect only response pulses meeting the specified amplitude threshold value, the offset adjustment can be helpful in reducing the sensitivity to illumination pulse temporal jitter, which might otherwise affect the determined "first differences" between averages of samples occurring during a response pulse (e.g., at 410) and averages of samples occurring between successive response pulses (e.g., at 412). An illustrative example of such offset adjusting a temporal offset such that an individual response pulse falls within a first time period representative of the illumination pulsewidth is described below.

At 602, a maximum amplitude value of the electrical response signal digitized samples obtained from the tissue sample 102 can be determined over the specified duration associated with a particular specified wavenumber. For example, for an example in which 6250 illumination pulses are issued during a specified duration of 10 milliseconds for a particular wavenumber step of a scan of 54 steps, this maximum amplitude value of the electrical response signal can be determined over the specified duration of 10 milliseconds.

At 604, a fourth central tendency (e.g., mean, median, or the like) of the digitized electrical response signal samples over the specified duration of 10 milliseconds associated with the particular specified wavenumber during the scan can be determined.

At 606, an offset detection amplitude threshold value can be established, such as at a specified fraction between the maximum response signal value determined at 602 and the fourth central tendency value determined at 604. For example, if the specified fraction is set to one-half, then the offset detection amplitude threshold value can be established at a midpoint between the maximum response signal value determined at 602 and the fourth central tendency value determined at 604.

At 608, an offset time between (1) a beginning of the specified duration of the specified wavenumber and (2) a time at which the response signal exceeds the offset detection amplitude threshold value can be determined, which can be used as an offset time for an individual response pulse, to initiate a time window of an expected illumination pulsewidth beginning at the determined offset-time. By aligning in this manner, samples in the offset-adjusted response pulse can be deemed to fall within the corresponding illumination pulse, such as for performing the averaging or other central tendency determination at 410. Such offset-adjustment can be carried out for each individual response pulse. The time corresponding to the beginning of the specified duration of the specified wavenumber can be determined by the control signal provided by the tunable light source 104 to the digital oscilloscope 116. Such a control signal is issued from the tunable light source 104 at each step between specified wavenumbers, such as seen in FIGS. 3A and 3B.

At 610, offset time determined at 608, for the specified wavenumber corresponding to the specified wavenumber step duration (e.g., 10 milliseconds) for that specified wavenumber can be used to offset-adjust a temporal offset such that an individual response pulse falls within a first time period (e.g., 50 nanoseconds) representative of an individual illumination pulsewidth. This temporal offset adjustment can be performed individually for each individual response pulse (e.g., of the 6250 pulses shown in the illustrative example of FIG. 3B) corresponding to an individual illumination pulse during the specified wavenumber step duration (e.g., 10 milliseconds).

Figure 7:
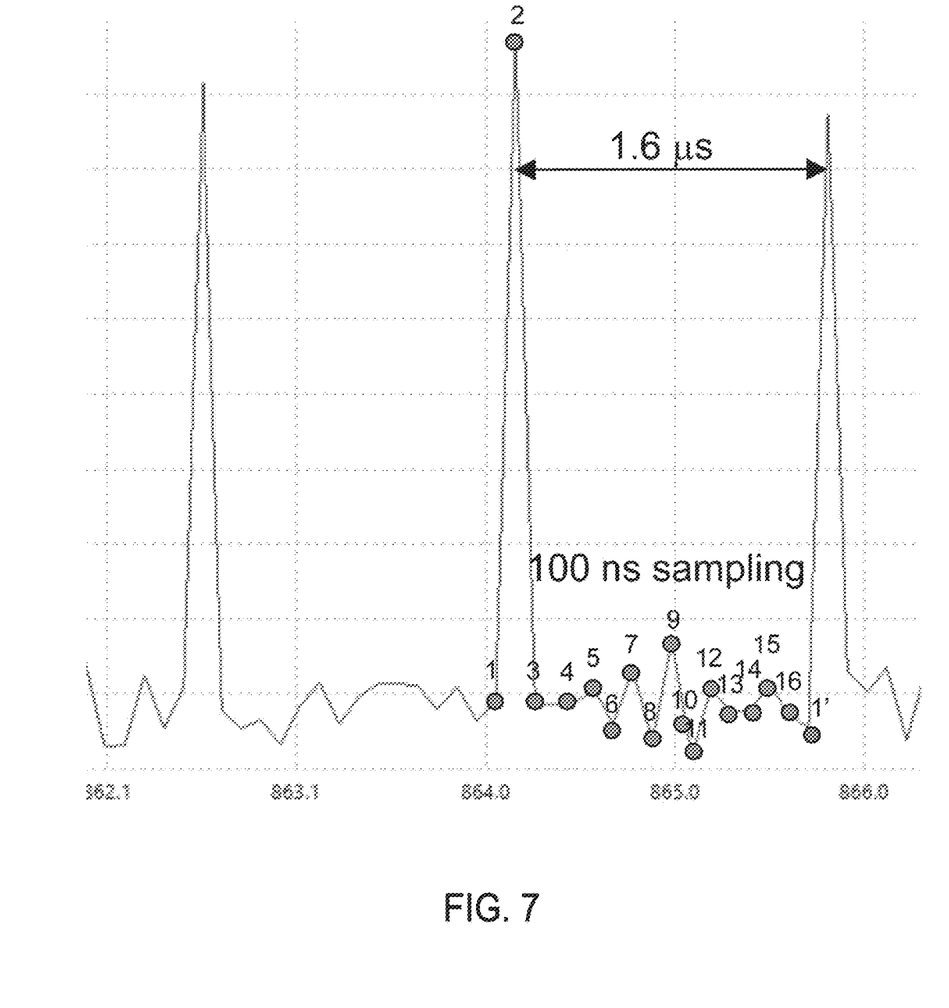
FIG. 7 is a conceptualized diagram illustrating portions of the technique described above with respect to FIG. 4.

FIG. 7 is a conceptualized diagram illustrating portions of the technique described above with respect to FIG. 4. FIG. 7 illustrates response signal amplitude vs. time for three successive electrical response pulses, together with illustrative sample points representing digitized electrical response signal samples. In the example of FIG. 7, sixteen digitized electrical response signal samples are shown, with samples 1-4 corresponding to the first time period (e.g., 400 nanoseconds, for these four samples separated from each other by 100 nanoseconds) of the offset-adjusted response pulse, and samples 9-12 corresponding to a similar first time period (e.g., 400 nanoseconds, for these four samples separated from each other by 100 nanoseconds) occurring between successive offset-adjusted response pulses. For each offset-adjusted electrical response pulse, a difference can be computed between (1) the average or other central tendency of samples 1-4 and (2) the average or other central tendency of samples 9-12. An average or other central tendency of these differences can be determined, such as over multiple ones or all of the electrical response pulses occurring during the specified duration (e.g., 10 milliseconds) of a specified wavenumber step, and used as a representative indication of the spectroscopic signal response from the tissue sample 102 at that specified wavenumber step. Such indications for multiple ones or each of the specified wavenumbers can be collectively used for spectroscopic analysis and characterization of the tissue sample 102, such as using the Support Vector Machines (SVM) technique or other analytic techniques such as described in Coe et al. U.S. Patent Application Publication No. US 2019/0110687 A1 entitled SYSTEM AND METHOD FOR THE DISCRIMINATION OF TISSUES USING A FAST INFRARED CANCER PROBE, which is incorporated herein by reference. The signal pre-processing described herein can help provide robust data that can accommodate amplitude and/or temporal variations in the illumination pulses issued by the tunable light source 104.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including"

and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform computer-assisted methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A computer-assisted method of using an electromagnetic energy illumination response signal from a tissue sample for spectroscopic analysis and tissue classification, the computer-assisted method comprising acts of:

(a) receiving samples of a response signal, including response pulses to electromagnetic energy illumination pulses delivered to the tissue sample over a specified duration;
    (b) determining a first central tendency of the samples over a first time period representative of an illumination pulsewidth;
    (c) determining a second central tendency of samples between response pulses over a second time period that is approximately equal to the first time period representative of the illumination pulsewidth;
    (d) determining a first difference between the first and second central tendencies for representing the response pulse; and
    (e) performing spectroscopic analysis, including at a specified wavenumber using the first difference, to classify the tissue sample.

2. The method of claim 1, comprising:

tuning a light source to the specified wavenumber to deliver a plurality of the electromagnetic energy illumination pulses over the specified duration; and
    detecting, transducing, and digitizing the samples of the response signal from the tissue sample during the specified duration.

3. The method of claim 2, wherein tuning a light source includes tuning a laser to a specified wavenumber to deliver a plurality of electromagnetic energy illumination pulses having a specified laser pulsewidth and a specified duty cycle at the specified wavenumber, within a specified wavenumber range, over a specified duration, including using a single tunable quantum cascade laser (QCL) to cover the specified wavenumber range.

4. The method of claim 2, wherein tuning a light source includes tuning a laser to a specified wavenumber to deliver a plurality of electromagnetic energy illumination pulses having a specified laser pulsewidth and a specified duty cycle at the specified wavenumber, within a specified wavenumber range, over a specified duration, including using multiple tunable quantum cascade lasers (QCLs) to cover the specified wavenumber range.

5. The method of claim 2, comprising delivering the plurality of electromagnetic energy illumination pulses to the tissue sample via an optical fiber and at least one of an Attenuated Total Reflectance (ATR) fiber loop probe or crystal tip.

6. The method of claim 2, wherein the light source comprises a tunable laser, and further comprising synchronizing the detecting and transducing the response signal from the tissue sample during the specified duration to a Start Scan control signal used by the laser to start a scan across different wavenumbers.

7. The method of claim 2, wherein the light source comprises a tunable laser, and further comprising synchronizing the detecting and transducing the response signal from the tissue sample during the specified duration to a Start Wavenumber Step control signal used by the laser to start issuing pulses at a specified wavenumber.

8. The method of claim 1, comprising:

digitally processing the samples to detect response pulses meeting a specified amplitude threshold value.

9. The method of claim 8, further comprising determining the specified amplitude threshold value by:

determining a pulse amplitude central tendency of response signal pulse amplitude of multiple response signal pulses respectively corresponding to individual pulses delivered to the tissue sample;

determining a noise floor central tendency amplitude between the response signal pulses; and determining the specified amplitude threshold value to be at a specified fraction between (1) the pulse amplitude central tendency of response signal pulse amplitude of the multiple response signal pulses and (2) the noise floor central tendency amplitude between the response signal pulses.

10. The method of claim 1, comprising:

offset-adjusting a temporal offset such that an individual response pulse falls within the first time period representative of an illumination pulsewidth, before the determining the first central tendency of the samples over the first time period representative of the illumination pulsewidth.

11. The method of claim 10, wherein offset-adjusting the temporal offset such that an individual response pulse falls within a first time period representative of the illumination pulsewidth, includes:

(g) determining a maximum response signal value from the tissue sample over the specified duration associated with the specified wavenumber;

(h) determining a fourth central tendency value of the response signal over the specified duration associated with the specified wavenumber;

(i) determining an offset detection amplitude threshold value at a specified fraction between the maximum response signal value and the fourth central tendency value;

(j) determining an offset time between a beginning of the specified duration and a time at which the response signal exceeds the offset detection amplitude threshold value; and (k) using the determined offset time, for the specified wavenumber corresponding to the specified duration, for offset-adjusting a temporal offset such that an individual response pulse falls within a first time period representative of the illumination pulsewidth.

12. The method of claim 11, comprising repeating (g) through (k) for different specified wavenumbers over corresponding respective different specified durations.

13. The method of claim 1, further comprising:

(f) determining a third central tendency of individual ones of the first differences corresponding to a plurality of the response pulses at the specified wavenumber for representing the response signal at the specified wavenumber, wherein the performing spectroscopic analysis, including at the specified wavenumber using the first difference, to classify the tissue sample, includes using the third central tendency of the first differences for the performing the spectroscopic analysis at the specified wavenumber to classify the tissue sample; and (g) repeating acts (a) through (f) over a plurality of wavenumbers within a specified wavenumber range to produce, and store in memory circuitry, a plurality of third central tendencies corresponding to respective specified wavenumbers in the specified wavenumber range.

14. The method of claim 1, wherein the electromagnetic energy illumination pulses are delivered at a duty cycle of less than or equal to 50 percent to limit accumulation of noise in the response signal between the electromagnetic energy illumination pulses.

15. The method of claim 14, wherein the electromagnetic energy illumination pulses are delivered at a duty cycle of less than or equal to 10 percent to limit accumulation of noise in the response signal between the electromagnetic energy illumination pulses.

16. The method of claim 15, wherein the electromagnetic energy illumination pulses are delivered at a duty cycle of about 5 percent to limit accumulation of noise in the response signal between the electromagnetic energy illumination pulses.

17. The method of claim 1, comprising using digital signal processing circuitry executing stored instructions for performing the digital signal processing, wherein the digital signal processing circuitry includes a digital oscilloscope including memory circuitry for storing the samples.

18. A system including one of processor circuitry or a device-readable medium for using an electromagnetic energy illumination response signal from a tissue sample for spectroscopic analysis and tissue classification, including or programmed with stored instructions that, when executed by processor circuitry, perform acts of:

(a) receiving samples of a response signal, including response pulses to electromagnetic energy illumination pulses delivered to the tissue sample over a specified duration;

(b) determining a first central tendency of the samples over a first time period representative of an illumination pulsewidth;

(c) determining a second central tendency of samples between response pulses over a second time period that is approximately equal to the first time period representative of the illumination pulsewidth;

(d) determining a first difference between the first and second central tendencies for representing the response pulse; and (e) performing spectroscopic analysis, including at a specified wavenumber using the first difference, to classify the tissue sample.

19. The system of claim 18, further including or programmed with stored instructions that, when executed by processor circuitry, perform the acts of:

(f) tuning a light source to the specified wavenumber to deliver a plurality of the electromagnetic energy illumination pulses over the specified duration;

(g) detecting, transducing, and digitizing the samples of the response signal from the tissue sample during the specified duration;

(h) digitally processing the samples to detect response pulses meeting a specified amplitude threshold value;

(i) offset-adjusting a temporal offset such that an individual response pulse falls within the first time period representative of an illumination pulsewidth, before the determining the first central tendency of the samples over the first time period representative of the illumination pulsewidth;

(j) determining a third central tendency of individual ones of the first differences corresponding to a plurality of the response pulses at the specified wavenumber for representing the response signal at the specified wavenumber, wherein the performing spectroscopic analysis, including at the specified wavenumber using the first difference, to classify the tissue sample, includes using the third central tendency of the first differences for the performing the spectroscopic analysis at the specified wavenumber to classify the tissue sample; and (k) repeating acts (a) through (j) over a plurality of wavenumbers within a specified wavenumber range to produce, and store in memory circuitry, a plurality of third central tendencies corresponding to respective specified wavenumbers in the specified wavenumber range; and wherein the electromagnetic energy illumination pulses are delivered at a duty cycle of less than or equal to 10 percent to limit accumulation of noise in the response signal between the electromagnetic energy illumination pulses.

20. A system including one of processor circuitry or a device-readable medium for using an electromagnetic energy illumination response signal from a tissue sample for spectroscopic analysis and tissue classification, including or programmed with stored instructions that, when executed by processor circuitry, perform acts of:
   (a) receiving samples of a response signal, including response pulses to electromagnetic energy illumination pulses delivered to the tissue sample over a specified duration at a duty cycle of less than 10 percent;
   (b) determining a first central tendency of the samples over a first time period representative of an illumination pulsewidth;
   (c) determining a second central tendency of samples between response pulses over a second time period that is approximately equal to the first time period representative of the illumination pulsewidth;
   (d) determining a first difference between the first and second central tendencies for representing the response pulse; and
   (e) performing spectroscopic analysis, including at a specified wavenumber using the first difference, to classify the tissue sample.

21. The system of claim 20, further including or programmed with stored instructions that, when executed by processor circuitry, perform the acts of:
   (f) tuning a light source to the specified wavenumber to deliver a plurality of the electromagnetic energy illumination pulses over the specified duration;
   (g) detecting, transducing, and digitizing the samples of the response signal from the tissue sample during the specified duration;
   (h) digitally processing the samples to detect response pulses meeting a specified amplitude threshold value;
   (i) offset-adjusting a temporal offset such that an individual response pulse falls within the first time period representative of an illumination pulsewidth, before the determining the first central tendency of the samples over the first time period representative of the illumination pulsewidth;
   (j) determining a third central tendency of individual ones of the first differences corresponding to a plurality of the response pulses at the specified wavenumber for representing the response signal at the specified wavenumber, wherein the performing spectroscopic analysis, including at the specified wavenumber using the first difference, to classify the tissue sample, includes using the third central tendency of the first differences for the performing the spectroscopic analysis at the specified wavenumber to classify the tissue sample; and
   (k) repeating acts (a) through (j) over a plurality of wavenumbers within a specified wavenumber range to produce, and store in memory circuitry, a plurality of third central tendencies corresponding to respective specified wavenumbers in the specified wavenumber range.

* * * * *